(12) United States Patent
Hogendijk et al.

(10) Patent No.: US 6,936,060 B2
(45) Date of Patent: Aug. 30, 2005

(54) APPARATUS AND METHODS FOR REMOVING EMBOLI DURING A SURGICAL PROCEDURE

(75) Inventors: Michael Hogendijk, Palo Alto, CA (US); Juan Carlos Parodi, Buenos Aires (AR)

(73) Assignee: Arteria Medical Sciences, Inc., San Francisco, CA (US)

( * ) Notice: Subject to any disclaimer, the term of this patent is extended or adjusted under 35 U.S.C. 154(b) by 274 days.

(21) Appl. No.: 10/100,628

(22) Filed: Mar. 14, 2002

(65) Prior Publication Data

US 2002/0151922 A1 Oct. 17, 2002

Related U.S. Application Data

(63) Continuation-in-part of application No. 09/418,727, filed on Oct. 15, 1999, now Pat. No. 6,423,032, which is a continuation-in-part of application No. 09/333,074, filed on Jun. 14, 1999, now Pat. No. 6,206,868, which is a continuation-in-part of application No. PCT/US99/05469, filed on Mar. 12, 1999, which is a continuation-in-part of application No. 09/078,263, filed on May 13, 1998, now Pat. No. 6,413,235.

(51) Int. Cl.[7] .................................. A61M 29/00
(52) U.S. Cl. .................. 606/200; 604/509; 604/96.01; 604/5.01
(58) Field of Search .............................. 604/96.01, 509, 604/101.04, 104, 5.01; 606/192, 200, 191, 194, 195

(56) References Cited

U.S. PATENT DOCUMENTS

| | | |
|---|---|---|
| 4,575,371 A | 3/1986 | Nordqvist et al. |
| 4,865,581 A | 9/1989 | Lundquist et al. |
| 4,921,478 A | 5/1990 | Solano et al. |
| 5,011,488 A | 4/1991 | Ginsburg |
| 5,584,803 A | 12/1996 | Stevens et al. |
| 5,765,568 A | 6/1998 | Sweezer, Jr. et al. |
| 5,794,629 A | 8/1998 | Frazee |
| 5,833,650 A | 11/1998 | Imran |
| 5,916,193 A | 6/1999 | Stevens et al. |
| 5,925,016 A | 7/1999 | Chornenky et al. |
| 6,022,336 A | 2/2000 | Zadno-Azizi et al. |
| 6,168,579 B1 | 1/2001 | Tsugita |
| 6,196,994 B1 | 3/2001 | Maahs |
| 6,290,689 B1 | 9/2001 | Delaney et al. |
| 6,295,989 B1 | 10/2001 | Connors, III |
| 6,383,172 B1 | 5/2002 | Barbut |
| 6,398,773 B1 | 6/2002 | Bagaoisan et al. |

Primary Examiner—Kevin C. Sirmons
(74) Attorney, Agent, or Firm—Nicola A. Pisano, Esq.; Luce, Forward, Hamilton & Scripps LLP

(57) ABSTRACT

Methods and apparatus for removing emboli during an endarterectomy procedure are provided. The present invention provides a proximal catheter disposed proximal to a stenosis and a distal catheter disposed distal to the stenosis. Each catheter may selectively communicate with a venous return catheter via a manifold having a setting controlled by a physician. Blood flows into an aspiration lumen of the distal catheter and is reperfused into a remote vein via the venous return catheter. Additionally, emboli generated during the procedure are removed via an aspiration lumen of the proximal catheter, and filtered blood then is reperfused into the remote vein.

33 Claims, 3 Drawing Sheets

APPARATUS AND METHODS FOR REMOVING EMBOLI DURING A SURGICAL PROCEDURE

REFERENCE TO RELATED APPLICATIONS

The present application is a continuation-in-part of U.S. patent application Ser. No. 09/418,727, filed Oct. 15, 1999 now U.S. Pat. No. 6,423,032, which is a continuation-in-part of U.S. patent application Ser. No. 09/333,074, filed Jun. 14, 1999, now U.S. Pat. No. 6,206,868, which is a continuation-in-part of International Application PCT/US99/05469, filed Mar. 12, 1999, which is a continuation-in-part of U.S. patent application Ser. No. 09/078,263, filed May 13, 1998 now U.S. Pat. No. 6,413,235.

FIELD OF THE INVENTION

This invention relates to apparatus and methods to protect against embolization during vascular interventions, such as endarterectomy. More particularly, the present invention reperfuses blood into a patient's venous vasculature and removes emboli using natural aspirational techniques.

BACKGROUND OF THE INVENTION

Carotid artery stenoses typically manifest in the common carotid artery, internal carotid artery or external carotid artery as a pathologic narrowing of the vascular wall, for example, caused by the deposition of plaque, that inhibits normal blood flow. Endarterectomy, an open surgical procedure, traditionally has been used to treat such stenosis of the carotid artery.

An important problem encountered in carotid artery surgery is that emboli may be formed during the course of the procedure, and these emboli can rapidly pass into the cerebral vasculature and cause ischemic stroke.

Several previously known apparatus and methods attempt to remove emboli formed during interventional procedures by trapping or suctioning the emboli out of the vessel of interest. These previously known systems, however, provide less than optimal solutions to the problems of effectively removing emboli.

It therefore would be desirable to provide methods and apparatus for removing emboli during surgical procedures, such as endarterectomy, that reduce the risk that emboli are carried into the cerebral vasculature.

It also would be desirable to provide methods and apparatus for removing emboli during surgical procedures that utilize natural aspiration techniques to minimize trauma imposed upon the treatment vessel.

It also would be desirable to provide methods and apparatus for removing emboli during a surgical procedure that enable filtering of emboli and reduced blood loss.

SUMMARY OF THE INVENTION

In view of the foregoing, it is an object of the present invention to provide methods and apparatus for removing emboli during surgical procedures, such as endarterectomy, that reduce the risk that emboli are carried into the cerebral vasculature.

It also is an object of the present invention to provide methods and apparatus for removing emboli during surgical procedures that utilize natural aspiration techniques to minimize trauma imposed upon the treatment vessel.

It is yet another object of the present invention to provide methods and apparatus for removing emboli during a surgical procedure that enable filtering of emboli and reduced blood loss.

The foregoing objects of the present invention are accomplished by providing apparatus comprising a proximal arterial catheter, a distal arterial catheter, a venous return catheter, and a manifold that allows the proximal and distal catheters to selectively communicate with the venous return catheter. The proximal and distal catheters each comprise proximal and distal ends, an aspiration lumen extending therethrough, an occlusion element disposed on the distal end, and a blood outlet port disposed at the proximal end that communicates with the aspiration lumen. The venous return catheter has proximal and distal ends, a lumen extending therethrough, and preferably comprises a filter element disposed between the proximal and distal ends. The venous return catheter further comprises a blood inlet port disposed at the proximal end and a blood outlet port disposed at the distal end.

The blood outlet port of the proximal catheter is coupled to a first intake port of the manifold, the blood outlet port of the distal catheter is coupled to a second intake port of the manifold, and the blood inlet port of the venous return catheter is coupled to an outlet port of the manifold. The manifold preferably comprises a valve that allows the proximal and distal catheters to selectively communicate with the venous return catheter.

In accordance with the principles of the present invention, the distal catheter is disposed in an artery just distal to a stenosis, e.g., by preparing a purse-string suture and making a stab incision in the artery, and the occlusion element is deployed. Similarly, the proximal arterial catheter is positioned at a location just proximal to the stenosis and the occlusion element of the proximal catheter is deployed to form an emboli containment chamber. Fluid communication between the venous return catheter and a remote vein then is established, e.g., by deploying a venous return sheath that is coupled to the distal end of the venous return catheter in the remote vein.

The manifold initially is set to permit fluid communication between the venous return catheter and the distal catheter. Negative pressure in the venous return catheter during diastole establishes a low rate continuous flow of blood through the aspiration lumen of the distal catheter that continues throughout the interventional procedure. An endarterectomy procedure then is performed and emboli that are generated are confined between the occlusion elements of the proximal and distal catheters, i.e., within the emboli containment chamber.

Upon completion of the endarterectomy procedure, the manifold setting is switched to permit fluid communication between the venous return catheter and the proximal arterial catheter, and the occlusion element of the distal arterial catheter is contracted. Emboli generated during the procedure then may be flushed into the aspiration lumen of the proximal catheter. Emboli preferably are removed via a filter disposed between the proximal and distal ends of the venous return catheter, and blood then is reperfused into the remote vein. Purse-string sutures may be used in conjunction with each of the three catheters to close the incisions upon removal of the respective catheters.

BRIEF DESCRIPTION OF THE DRAWINGS

Further features of the invention, its nature and various advantages will be more apparent from the accompanying drawings and the following detailed description of the preferred embodiments, in which.

DESCRIPTION OF THE PREFERRED EMBODIMENTS

Figure 1:
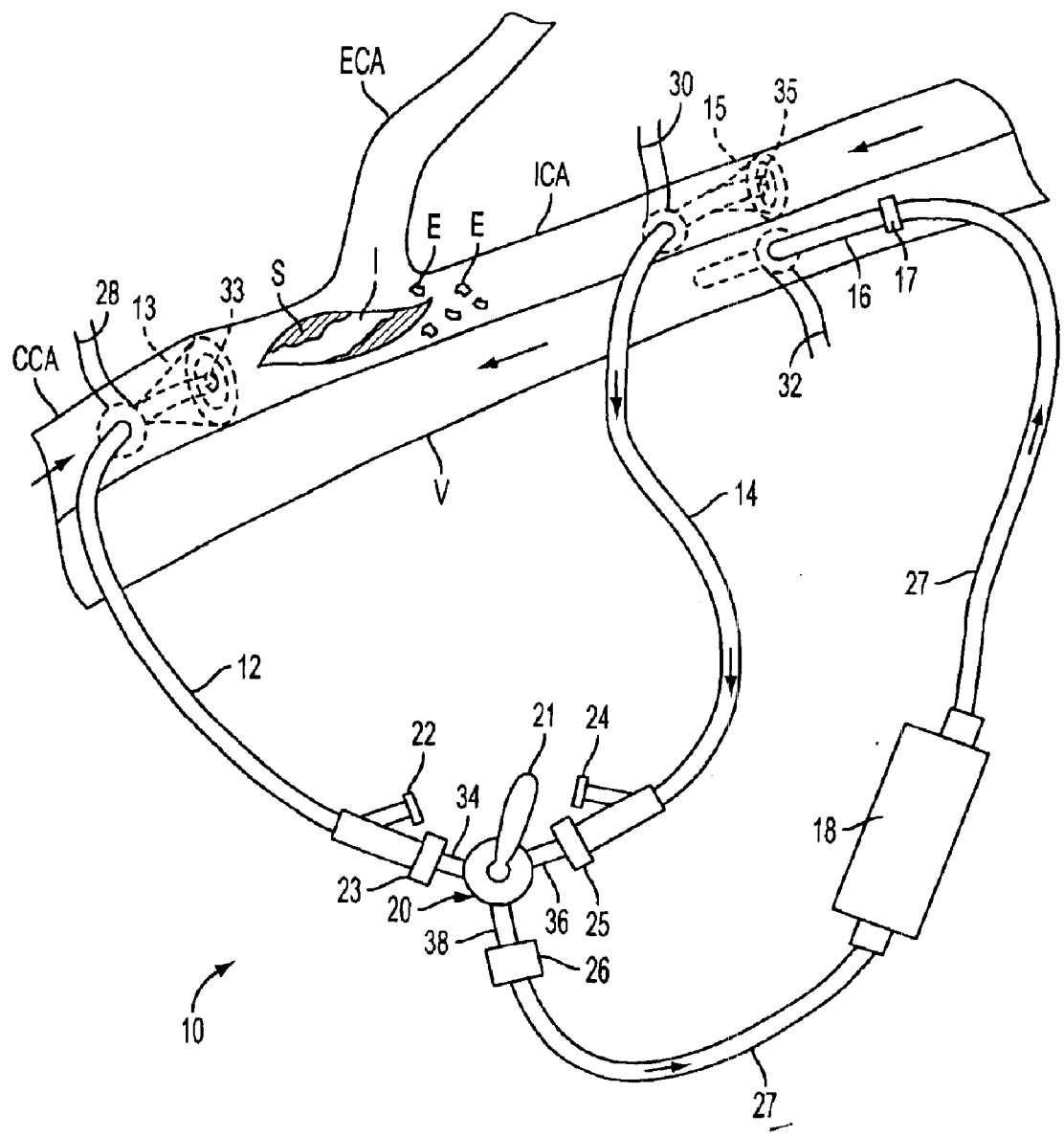
FIG. 1 is a schematic view of the embolic protection system of the present invention.

Referring to FIG. 1, a schematic view of the emboli removal system of the present invention is described. Emboli removal apparatus 10 comprises proximal catheter 12, distal catheter 14 and venous return catheter 27. In accordance with principles of the present invention, proximal and distal catheters 12 and 14 selectively may communicate with venous return catheter 27, for example, using manifold 20 having multi-position valve 21.

Proximal catheter 12 has proximal and distal ends, and aspiration lumen 33 extending therethrough. Proximal catheter 12 further comprises occlusion element 13, e.g., a balloon, disposed at the distal end, and inflation port 22 disposed at the proximal end that communicates with occlusion element 13 via an inflation lumen of catheter 12, details of which are described with respect to FIG. 3D hereinbelow. Proximal catheter 12 further comprises blood outlet port 23 at the proximal end that communicates with aspiration lumen 33 and is coupled to first intake port 34 of manifold 20.

Distal catheter 14 similarly has proximal and distal ends, and aspiration lumen 35 extending therethrough. Distal catheter 14 further comprises occlusion element 15, e.g., a balloon, disposed at the distal end, and inflation port 24 disposed at the proximal end that communicates with occlusion element 15 via an inflation lumen of catheter 14. Distal catheter 14 further comprises blood outlet port 25 at the proximal end that communicates with aspiration lumen 35 and is coupled to second intake port 36 of manifold 20. A detailed description of the preferred features of proximal catheter 12 and distal catheter 14 are described with respect to FIG. 3 hereinbelow.

Venous return catheter 27 has proximal and distal ends, and a lumen extending therethrough. Venous return catheter 27 preferably comprises blood inlet port 26 disposed at the proximal end that communicates with the lumen of venous return catheter 27, and further is coupled to outlet port 38 of manifold 20. Venous return catheter 27 further preferably comprises blood outlet port 17 disposed at the distal end that communicates with a patient's venous vasculature, e.g., by coupling blood outlet port 17 to venous return sheath 16, which in turn is adapted to be inserted into a patient's venous system. Filter 18 optionally may be disposed between blood inlet port 26 of venous return catheter 27 and blood outlet port 17.

In a first step, purse-string suture 30 is made in an artery at a location distal to stenosis S. As illustrated in FIG. 1, purse-string suture 30 is made in internal carotid artery ICA for a stenosis located near the carotid bifurcation. It will be apparent to those skilled in the art that such purse-string sutures similarly may be disposed elsewhere for stenoses located in other vasculature.

A stab incision then is made and distal catheter 14 is inserted over a short guidewire and dilator (not shown) so that the distal end is positioned distal to stenosis S. Occlusion element 15 then is deployed, for example, by inflating occlusion element 15 via inflation port 24 and an inflation lumen of distal catheter 14. Air is purged from distal catheter 14 and blood outlet port 25 is coupled to second intake port 36 of manifold 20.

Proximal catheter 12 then is deployed in a manner similar to that of distal catheter 14. Purse-string suture 28 is made in an artery proximal to stenosis S. In FIG. 1, purse-string suture 28 is disposed in the common carotid artery CCA for a stenosis located near the carotid bifurcation. A stab incision is made and proximal catheter 12 then may be inserted over a short guidewire and dilator (not shown) so that the distal end is positioned just proximal to stenosis S. Occlusion element 13 is deployed via inflation port 22 to occlude antegrade flow in the artery proximal to occlusion element 13, as shown in FIG. 1. Air is purged from proximal catheter 12 and blood outlet port 23 is coupled to first intake port 34 of manifold 20.

Next, purse-string suture 32 is made in a remote vein V, e.g., the jugular vein. A distal end of venous return sheath 16 is disposed in remote vein V and a proximal end of venous return sheath 16 is coupled to blood outlet port 17 of venous return catheter 27, as shown in FIG. 1. Blood outlet port 38 of manifold 20 then is coupled to blood inlet port 26 of catheter 27. Alternatively, blood outlet port 38 of manifold 20 and blood outlet port 17 of catheter 27 may be lengthened to engage either end of filter 18 or each other. A conventional cross-clamp may be applied to external carotid artery ECA to prevent retrograde flow into the operative field. When occlusion elements 13 and 15 of catheters 12 and 14, respectively, are deployed, and the ECA is cross-clamped, longitudinal incision I may be made in the area of the stenosis and an endarterectomy procedure performed in accordance with well-known methods.

Valve 21 of manifold 20 initially is set so that venous return catheter 27 communicates solely with aspiration lumen 35 of distal catheter 14. Once distal catheter 14 and venous return catheter 27 are coupled to manifold 20 as described hereinabove, negative pressure in venous return catheter 27 during diastole will establish a low rate continuous flow of blood through aspiration lumen 35 of distal catheter 14, while maintaining the operative field substantially free of blood.

This low rate continuous flow due to the difference between venous pressure and arterial pressure will continue throughout the procedure. Specifically, blood passes through aspiration lumen 35 and blood outlet port 25 of distal catheter 14, through second intake port 36 of manifold 20, through outlet port 38 of manifold 20, through blood inlet port 26, and through venous return catheter 27 and/or filter 18. Then, blood passes through outlet port 17 of venous return catheter 27, where it is reperfused into the remote vein, as illustrated by the direction of the arrows in FIG. 1.

Continuous blood flow with reperfusion in accordance with the present invention provides efficient emboli removal with significantly reduced blood loss. Alternatively, filter 18 may be omitted, in which case emboli removed from the arterial side will be introduced in the venous side and eventually captured in the lungs.

With reperfused blood flow from distal catheter 14 into venous return catheter 27, an endarterectomy procedure then may be performed, e.g., by creating access incision I and removing or dislodging stenosis S. The endarterectomy procedure may generate emboli E, which are confined to an emboli containment chamber formed between occlusion elements 13 and 15.

Figure 2:
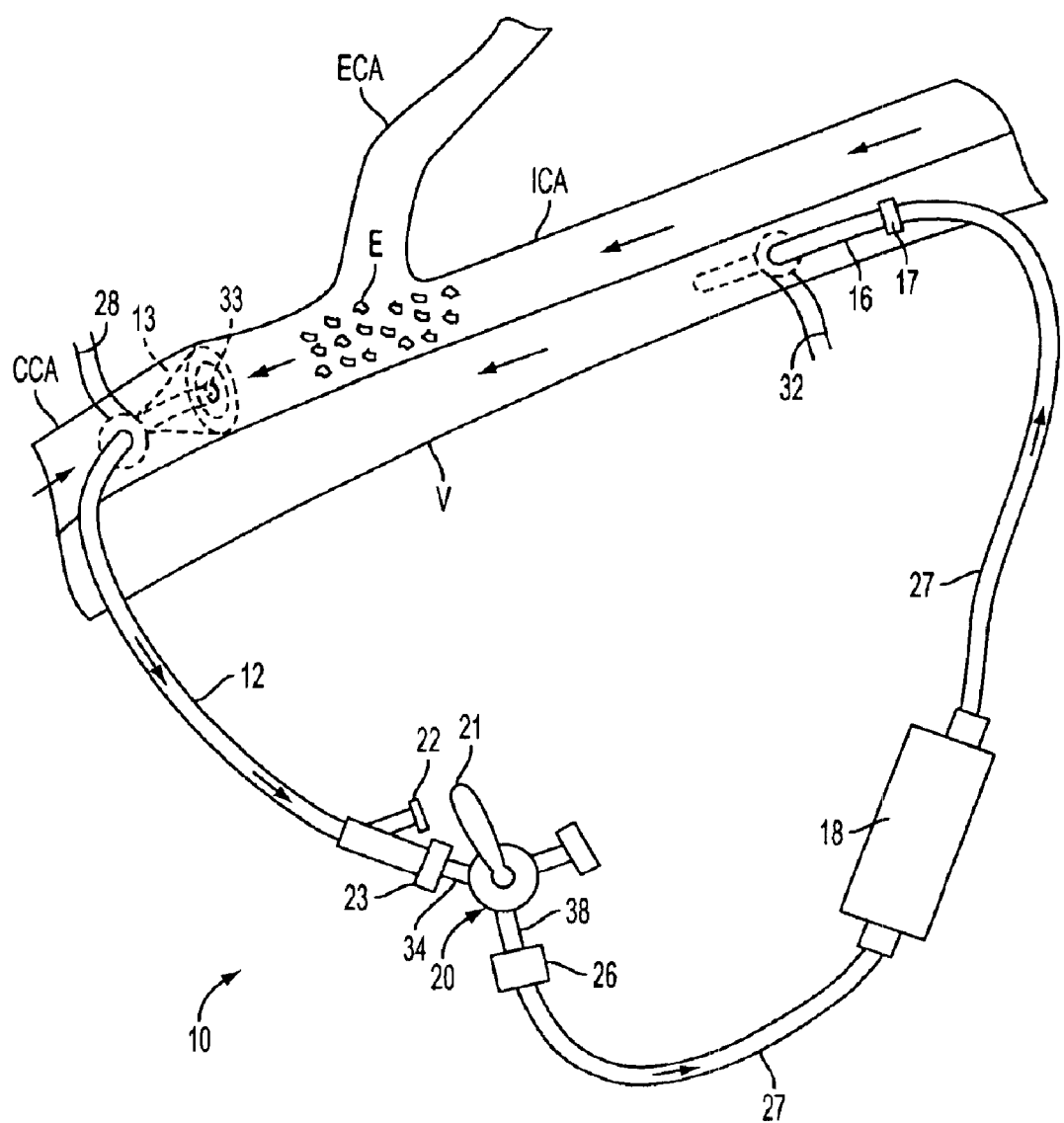
FIG. 2 is a second schematic view of the embolic protection system of the present invention wherein a proximal catheter is used to removal emboli.

Upon satisfactory removal or disruption of stenosis S, access incision I then is closed, e.g., by suturing. Valve 21 of manifold 20 then is set to a second position whereby aspiration lumen 33 of proximal catheter 12 communicates solely with venous return catheter 27, as shown in FIG. 2. Occlusion element 15 is contracted and distal catheter 14 is removed from the patient's artery, with purse-string suture 30 being secured to seal the artery.

The difference between venous pressure from venous catheter 27 and arterial pressure from proximal catheter 12 will cause blood and emboli E to be directed into aspiration lumen 33 of proximal catheter 12, as indicated by the arrows in FIG. 2. Blood and emboli E pass through aspiration lumen 33 and blood outlet port 23 of proximal catheter 12, through first intake port 34 of manifold 20, through outlet port 38 of manifold 20, through inlet port 26, through venous return catheter 27 and/or filter 18, and then through blood outlet port 17 and into remote vein V. When emboli are filtered using filter 18, filtered blood may be reperfused into remote vein V, as shown in FIG. 2.

Flow reversal in the artery will be maintained for a period sufficient to ensure removal of emboli E generated during the procedure. Upon satisfactory emboli removal, occlusion element 13 is contracted and proximal catheter 12 is removed from the patient's artery. Purse-string suture 28 then is secured, and venous return sheath 16 then is removed from remote vein V and purse-string suture 32 is secured.

Unlike the previously known naturally-aspirated systems, the present invention provides substantially continuous retrograde blood flow through the artery while preventing blood from flowing antegrade and preventing emboli from being carried into the cerebral vasculature. Because the apparatus and methods of the present invention "recycle" emboli-laden blood from the arterial catheters through the blood filter and to the venous return catheter, the patient experiences significantly less blood loss.

Referring now to FIG. 3, a preferred design for both proximal catheter 12 and distal catheter 14 is provided. In FIG. 3A, arterial catheter 41 comprises distal occlusion element 42, blood outlet port 43, inflation port 44, and aspiration lumen 58.

Figure 3A:
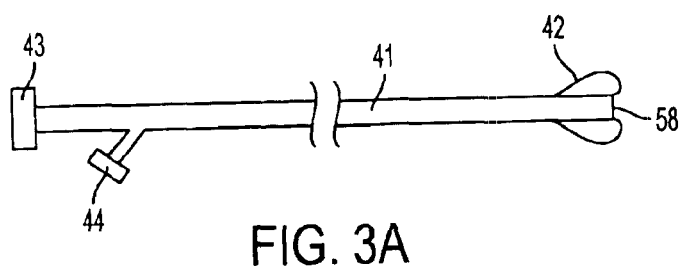
FIGS. 3A-3D are, respectively, a schematic view, and detailed side and sectional views of the distal end of an embolic removal catheter of the present invention.
Figure 3B:
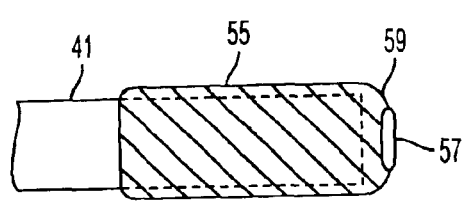
Figure 3C:
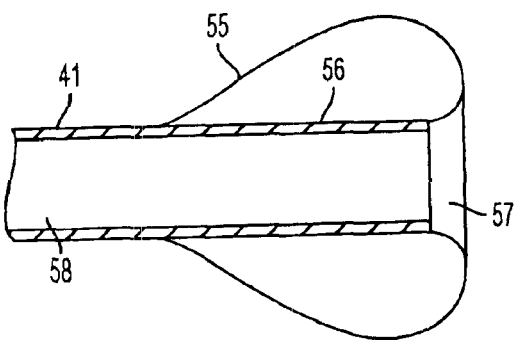

With respect to FIGS. 3B and 3C, distal occlusion element 42 comprises expandable bell or pear-shaped balloon 55. In accordance with manufacturing techniques which are known in the art, balloon 55 comprises a compliant material, such as polyurethane, latex or polyisoprene which has variable thickness along its length to provide a bell-shape when inflated. Balloon 55 is affixed to distal end 56 of catheter 41, for example, by gluing or a melt-bond, so that opening 57 in balloon 55 leads into aspiration lumen 58 of catheter 41. Balloon 55 preferably is wrapped and heat treated during manufacture so that distal portion 59 of the balloon extends beyond the distal end of catheter 41 and provides an atraumatic tip or bumper for the catheter.

Figure 3D:
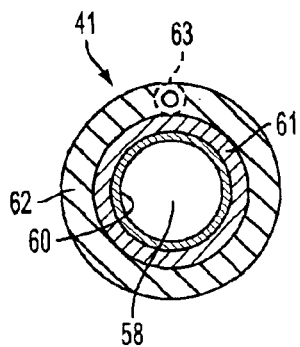

As shown in FIG. 3D, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 44 to balloon 55.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. Apparatus for removing emboli during an endarterectomy procedure, the apparatus comprising:
   a proximal catheter having proximal and distal ends, an aspiration lumen extending therethrough, a blood outlet port at the proximal end, and an occlusion element disposed on the distal end;
   a distal catheter having proximal and distal ends, an aspiration lumen extending therethrough, a blood outlet port at the proximal end, and an occlusion element disposed on the distal end;
   a venous return catheter having proximal and distal ends, a lumen extending therethrough, and a blood inlet port in communication with the lumen, a blood outlet port disposed at the distal end;
   a venous return sheath having a first end coupled to the blood outlet port of the venous return catheter and a second end adapted to be inserted into a patient's venous vasculature; and
   a manifold including a valve having a first position configured to selectively permit fluid communication between the proximal catheter and venous return catheter, and between a second position configured to permit fluid communication between the distal catheter and the venous return catheter.

2. The apparatus of claim 1 wherein the manifold comprises a first intake port in fluid communication with the blood outlet port of the proximal catheter.

3. The apparatus of claim 2 wherein the manifold comprises a second intake port in fluid communication with the blood outlet port of the distal catheter.

4. The apparatus of claim 3 wherein the manifold comprises an outlet port in fluid communication with the blood inlet port of the venous return catheter.

5. The apparatus of claim 1 further comprising a filter disposed between the proximal and distal ends of the venous return catheter.

6. The apparatus of claim 1 wherein the occlusion element of the distal catheter is a balloon.

7. The apparatus of claim 6 wherein the distal catheter further comprises an inflation port at the proximal end and an inflation lumen that permits fluid communication between the inflation port and the balloon.

8. The apparatus of claim 1 wherein the occlusion element of the proximal catheter is a balloon.

9. The apparatus of claim 8 wherein the proximal catheter further comprises an inflation port at the proximal end and an inflation lumen that permits fluid communication between the inflation port and the balloon.

10. The apparatus of claim 1 wherein the venous return catheter further comprises a blood outlet port disposed at the distal end that is coupled to a venous return sheath, wherein the venous return sheath is adapted to be inserted into a patient's venous vasculature.

11. A method for removing emboli during an endarterectomy procedure, the method comprising:
   providing a distal catheter having proximal and distal ends, an aspiration lumen extending therethrough, a blood outlet port coupled to the lumen, and an occlusion element disposed on the distal end;
   providing a proximal catheter having proximal and distal ends, an aspiration lumen extending therethrough, a blood outlet port coupled to the lumen, and an occlusion element disposed on the distal end;
   providing a venous return catheter having proximal and distal ends, a lumen extending therethrough, and a blood inlet port coupled to the lumen;

inserting the distal end of the distal catheter into a vessel to a position distal to a stenosis;

inserting the distal end of the proximal catheter into a vessel to a position proximal to the stenosis;

establishing fluid communication between the venous return catheter and a remote vein;

deploying the occlusion element of the distal catheter and the occlusion element of the proximal catheter;

selectively permitting fluid communication between the distal catheter and the venous return catheter;

selectively permitting fluid communication between the proximal catheter and the venous return catheter; and performing a surgical procedure to treat the stenosis, wherein emboli that are generated during the surgical procedure are confined to an area between the occlusion element of the proximal catheter and the occlusion element of the distal catheter.

12. The method of claim 11 wherein permitting fluid communication between the distal catheter and the venous return catheter causes blood to flow between the blood outlet port of the distal catheter and the blood inlet port of the venous return catheter to induce reverse flow in the vessel.

13. The method of claim 12 wherein a manifold is used to selectively control fluid communication between the distal catheter and the venous return catheter.

14. The method of claim 11 wherein permitting fluid communication between the proximal catheter and the venous return catheter causes blood and emboli to flow into the aspiration lumen of the proximal catheter and through the blood inlet port of the venous return catheter.

15. The method of claim 14 wherein a manifold is used to selectively control fluid communication between the proximal catheter and the venous return catheter.

16. The method of claim 14 wherein emboli are filtered and blood is reperfused into the venous return catheter.

17. Apparatus for removing emboli during an endarterectomy procedure, the apparatus comprising:

a proximal catheter having proximal and distal ends, an aspiration lumen extending therethrough, a blood outlet port at the proximal end, and an occlusion element disposed on the distal end;

a distal catheter having proximal and distal ends, an aspiration lumen extending therethrough, a blood outlet port at the proximal end, and an occlusion element disposed on the distal end;

a venous return catheter having proximal and distal ends, a lumen extending therethrough, and a blood inlet port in communication with the lumen; and a manifold configured to selectively permit fluid communication between the proximal catheter and venous return catheter, and between the distal catheter and the venous return catheter, the manifold further comprising a valve configured, in a first position, to selectively permit fluid communication solely between the proximal catheter and the venous return catheter.

18. The apparatus of claim 17 wherein the manifold comprises a first intake port in fluid communication with the blood outlet port of the proximal catheter.

19. The apparatus of claim 18 wherein the manifold comprises a second intake port in fluid communication with the blood outlet port of the distal catheter.

20. The apparatus of claim 19 wherein the manifold comprises an outlet port in fluid communication with the blood inlet port of the venous return catheter.

21. The apparatus of claim 17 further comprising a filter disposed between the proximal and distal ends of the venous return catheter.

22. The apparatus of claim 17 wherein the valve further is configured, in a second position, to permit fluid communication solely between the distal catheter and the venous return catheter.

23. The apparatus of claim 17 wherein the occlusion element of the distal catheter is a balloon.

24. The apparatus of claim 23 wherein the distal catheter further comprises an inflation port at the proximal end and an inflation lumen that permits fluid communication between the inflation port and the balloon.

25. The apparatus of claim 17 wherein the occlusion element of the proximal catheter is a balloon.

26. The apparatus of claim 25 wherein the proximal catheter further comprises an inflation port at the proximal end and an inflation lumen that permits fluid communication between the inflation port and the balloon.

27. A method for removing emboli during an endarterectomy procedure, the method comprising:

providing a distal catheter having proximal and distal ends, an aspiration lumen extending therethrough, a blood outlet port coupled to the lumen, and an occlusion element disposed on the distal end;

providing a proximal catheter having proximal and distal ends, an aspiration lumen extending therethrough, a blood outlet port coupled to the lumen, and an occlusion element disposed on the distal end;

providing a venous return catheter having proximal and distal ends, a lumen extending therethrough, and a blood inlet port coupled to the lumen;

inserting the distal end of the distal catheter into a vessel to a position distal to a stenosis;

inserting the distal end of the proximal catheter into a vessel to a position proximal to the stenosis;

establishing fluid communication between the venous return catheter and a remote vein;

deploying the occlusion element of the distal catheter and the occlusion element of the proximal catheter;

selectively permitting fluid communication between the distal catheter and the venous return catheter; and selectively permitting fluid communication between the proximal catheter and the venous return catheter, wherein permitting fluid communication between the proximal catheter and the venous return catheter causes blood and emboli to flow into the aspiration lumen of the proximal catheter and through the blood inlet port of the venous return catheter.

28. The method of claim 27 wherein permitting fluid communication between the distal catheter and the venous return catheter causes blood to flow between the blood outlet port of the distal catheter and the blood inlet port of the venous return catheter to induce reverse flow in the vessel.

29. The method of claim 28 wherein a manifold is used to selectively control fluid communication between the distal catheter and the venous return catheter.

30. The method of claim 27 further comprising performing a surgical procedure to treat the stenosis.

31. The method of claim 30 wherein emboli that are generated during the surgical procedure are confined to an area between the occlusion element of the proximal catheter and the occlusion element of the distal catheter.

32. The method of claim 27 wherein a manifold is used to selectively control fluid communication between the proximal catheter and the venous return catheter.

33. The method of claim 27 wherein emboli are filtered and blood is reperfused into the venous return catheter.

* * * * *